United States Patent [19]

Stewart et al.

[11] Patent Number: 4,621,062
[45] Date of Patent: Nov. 4, 1986

[54] CONTROL OF AN ISOMERIZATION PROCESS

[75] Inventors: William S. Stewart; John E. Blaesi, both of Bartlesville, Okla.

[73] Assignee: Phillips Petroleum Company, Bartlesville, Okla.

[21] Appl. No.: 604,810

[22] Filed: Apr. 27, 1984

[51] Int. Cl.[4] .................. G01N 35/00; G05B 1/00; G05B 1/06; G05B 23/00
[52] U.S. Cl. .................. 436/55; 364/500; 422/62; 422/108; 422/110; 422/111; 585/734
[58] Field of Search ............ 422/62, 108, 110, 117; 436/55; 585/734; 364/500

[56] References Cited

U.S. PATENT DOCUMENTS

| | | | |
|---|---|---|---|
| 3,271,467 | 9/1966 | Nakayama | 260/666 |
| 3,649,202 | 3/1972 | Bajek et al. | 364/500 |
| 3,751,229 | 8/1973 | Bajek et al. | 208/139 |
| 3,981,792 | 9/1976 | Scott | 203/49 |
| 4,039,604 | 8/1977 | Myers et al. | 260/666 P |
| 4,129,606 | 12/1978 | Gowartowski | 208/260 |
| 4,217,244 | 8/1980 | Montgomery | 252/419 |
| 4,228,509 | 10/1980 | Kennedy | 208/133 X |
| 4,249,908 | 2/1981 | Funk | 364/500 X |

OTHER PUBLICATIONS

Cartwright et al, "C$_5$/C$_6$ Isomerization", *Hydrocarbon Processing*, Sep. 1982, p. 170.

*Primary Examiner*—Barry S. Richman
*Assistant Examiner*—William R. Johnson
*Attorney, Agent, or Firm*—George E. Bogatie

[57] ABSTRACT

Control of an isomerization process is based on a known relationship between the octane number and temperature of a reaction at equilibrium; and a predetermined relationship between octane number and temperature of the reaction product of a reactor using a specific catalyst. In use, measurements of actual octane number and temperature are compared with the octane number and temperature of a reaction at equilibrium to determine if the reaction is at equilibrium. If the reaction is not at equilibrium, a control signal is developed to restore equilibrium. Thus control of an isomerization process is accomplished so as to substantially maximize the efficiency of the isomerization process both from a production standpoint and from an energy usage standpoint by maintaining the isomerization reaction at desired equilibrium conditions. Also, for a dual reactor system, the differential temperature between the two reactors is manipulated so as to maintain more favorable isomerization conditions in the tail reactor. Energy efficiency is improved by substantially minimizing the amount of heating fluid utilized to preheat the feed to the isomerization process.

20 Claims, 4 Drawing Figures

CONTROL OF AN ISOMERIZATION PROCESS

This invention relates to control of an isomerization process. In one aspect, this invention relates to method and apparatus for controlling an isomerization process so as to substantially maximize the efficiency of the isomerization process both from a production standpoint and from an energy usage standpoint.

Isomerization refers to a process which is conventionally used to convert normal $C_5$, $C_6$ and $C_7$ paraffins to isomers for octane improvement. The process is typically used to produce high octane gasoline blending components which can be utilized to increase the octane of gasoline.

As with any chemical manufacturing process, it is desirable to substantially maximize the production of the desired product while substantially minimizing the energy used by the process. It is an object of this invention to provide an interactive control system for an isomerization process which substantially maximizes the efficiency of the isomerization process both from a production standpoint and from an energy usage standpoint.

In accordance with the present invention, method and apparatus is provided whereby the production of the desired isomers is optimized by maintaining the isomerization reaction at desired equilibrium conditions. Also, for a dual reactor system, the differential temperature between the two reactors is manipulated so as to maintain more favorable isomerization conditions in the tail reactor. Energy efficiency is improved by substantially minimizing the amount of heating fluid utilized to preheat the feed to the isomerization process. All of the above control is accomplished while not violating any process constraints.

Other objects and advantages of the invention will be apparent from the foregoing brief description of the invention and the claims as well as from the detailed description of the drawings which are briefly described as follows:

The invention is described in terms of an isomerization process employing two reactors. However, parts of the invention could be applied to an isomerization process using only one reactor if desired as will be more fully described hereinafter.

Figure 1:
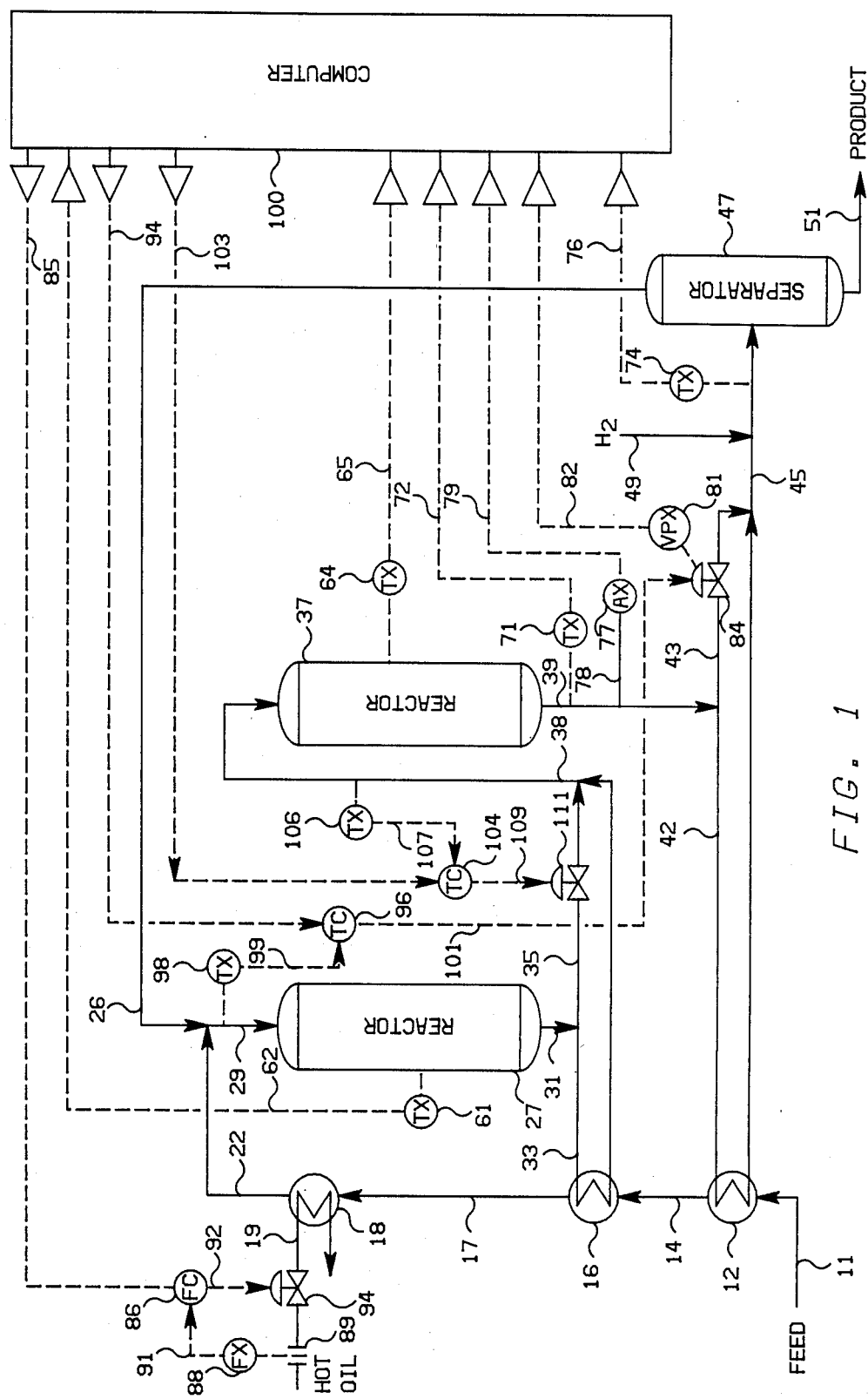
FIG. 1 is a diagrammatic illustration of an isomerization process employing two reactors and the associated control system of the present invention.

A specific control system configuration is set forth in FIG. 1 for the sake of illustration. However, the invention extends to different types of control system configurations which accomplish the purpose of the invention. Lines designated as signal lines in the drawings are electrical or pneumatic in this preferred embodiment. Generally, the signals provided from any transducer are electrical in form. However, the signals provided from flow sensors will generally be pneumatic in form. Transducing of these signals is not illustrated for the sake of simplicity because it is well known in the art that, if a flow is measured in pneumatic form, it must be transduced to electrical form if it is to be transmitted in electrical form by a flow transducer. Also, transducing of the signals from analog form to digital form or from digital form to analog form is not illustrated because such transducing is also well known in the art.

The invention is also applicable to mechanical, hydraulic or other signal means for transmitting information. In almost all control systems some combination of electrical, pneumatic, mechanical or hydraulic signals will be used. However, use of any other type of signal transmission, compatible with the process and equipment in use, is within the scope of the invention.

A digital computer is used in the preferred embodiment of this invention to calculate the required control signals based on measured process parameters as well as set points supplied to the computer. Analog computers or other types of computing devices could also be used in the invention. The digital computer is preferably an OPTROL 7000 Process Computer System from Applied Automation, Inc., Bartlesville, Okla.

Signal lines are also utilized to represent the results of calculations carried out in a digital computer and the term "signal" is utilized to refer to such results. Thus, the term signal is used not only to refer to electrical currents or pneumatic pressures but is also used to refer to binary representations of a calculated or measured value.

The controllers shown may utilize the various modes of control such as proportional, proportional-integral, proportional-derivative, or proportional-integral-derivative. In this preferred embodiment, proportional-integral-derivative controllers are utilized but any controller capable of accepting two input signals and producing a scaled output signal, representative of a comparison of the two input signals, is within the scope of the invention.

The scaling of an output signal by a controller is well known in control system art. Essentially, the output of a controller may be scaled to represent any desired factor or variable. An example of this is where a desired flow rate and an actual flow rate is compared by a controller. The output could be a signal representative of a desired change in the flow rate of some gas necessary to make the desired and actual flows equal. On the other hand, the same output signal could be scaled to represent a percentage or could be scaled to represent a temperature change required to make the desired and actual flows equal. If the controller output can range from 0 to 10 volts, which is typical, then the output signal could be scaled so that an output signal having a voltage level of 5.0 volts corresponds to 50 percent, some specified flow rate, or some specified temperature.

The various transducing means used to measure parameters which characterize the process and the various signals generated thereby may take a variety of forms or formats. For example, the control elements of the system can be implemented using electrical analog, digital electronic, pneumatic, hydraulic, mechanical or other similar types of equipment or combinations of one or more such equipment types. While the presently preferred embodiment of the invention preferably utilizes a combination of pneumatic final control elements in conjunction with electrical analog signal handling and translation apparatus, the apparatus and method of the invention can be implemented using a variety of specific equipment available to and understood by those skilled in the process control art. Likewise, the format of the various signals can be modified substantially in order to accommodate signal format requirements of the particular installation, safety factors, the physical characteristics of the measuring or control instruments and other similar factors. For example, a raw flow measurement signal produced by a differential pressure orifice flow meter would ordinarily exhibit a generally proportional relationship to the square of the actual flow rate. Other measuring instruments might produce a signal which is proportional to the measured parameter, and still other transducing means may produce a signal which bears a more complicated, but known, relationship to the measured parameter. Regardless of the signal format or the exact relationship of the signal to the parameter which it represents, each signal representative of a measured process parameter or representative of a desired process value will bear a relationship to the measured parameter or desired value which permits designation oi a specific measured or desired value by a specific signal value. A signal which is representative of a process measurement or desired process value is therefore one from which the information regarding the measured or desired value can be readily retrieved regardless of the exact mathematical relationship between the signal units and the measured or desired process units.

Referring now to the drawings and in particular to FIG. 1, a feed which would typically be pentanes or hexanes or a mixture of the two is provided through conduit 11 to the heat exchanger 12. The feed flowing through conduit 11 is removed from heat exchanger 12 through conduit 14 and is provided to heat exchanger 16. The feed flowing through conduit 14 is removed from heat exchanger 16 through conduit 17 and is provided to heat exchanger 18. The heat exchanger 18 is provided with a heating fluid such as hot oil which flows through conduit 19.

The feed flowing through conduit 17 is removed from the heat exchanger 18 through conduit 22. The feed flowing through conduit 22 is combined with a recycle stream flowing through conduit 26, as will be described more fully hereinafter, and the resulting combination is provided as a feed to the reactor 27 through conduit 29.

The reactor 27 will typically contain a platinum-based catalyst. The feed flowing through conduit 29 is passed in contact with the catalyst contained In reactor 27 to at least partially isomerize the feed flowing through conduit 29 and the resulting reaction effluent is withdrawn from reactor 27 through conduit 31.

A first portion of the reaction effluent flowing through conduit 31 is provided through conduit 33 as a heating fluid to the heat exchanger 16. A second portion of the reaction effluent flowing through conduit 31 flows through conduit 35. The reaction effluent flowing through conduit 33 and conduit 35 is combined and is provided as a feed to the reactor 37 through conduit 38.

As was the case with reactor 27, reactor 37 will typically contain a platinum-based catalyst. The feed flowing through conduit 38 is passed in contact with the catalyst contained in reactor 37 and further isomerization occurs at more favorable isomerization conditions. The reaction effluent from reactor 37 is withdrawn through conduit 39.

A first portion of the reaction effluent flowing through conduit 39 is provided through conduit 42 as a heating fluid to the heat exchanger 12. A second portion of the reaction effluent withdrawn through conduit 39 flows through conduit 43. The fluids flowing through conduit 42 and 43 are combined and the resulting combination is provided through conduit 45 to the separator 47. Hydrogen is also added through conduit 49 to the fluid flowing through conduit 45. This hydrogen is utilized in the isomerization reaction.

A liquid product which contains a high concentration of isomers is withdrawn through conduit 51 from the separator 47. Gases including hydrogen are withdrawn from the separator 47 through conduit 26 and are recycled to reactor 27 as has been previously described.

The isomerization process described to this point is a conventional isomerization process. Other streams would typically be present such as an organic fluoride makeup which is sometimes utilized to improve the activity of the catalyst. However, such other streams have not been illustrated for the sake of simplicity because these other streams are well known to those skilled in the art and these other streams play no part in the description of the present invention. Also, additional equipment such as pumps, additional heat exchangers, compressors, additional control components, etc. which would typically be associated with an isomerization process have not been illustrated since these additional components play no part in description of the present invention.

In general, control of the isomerization process in accordance with the present invention is accomplished by using process measurements to establish three control signals. The process measurements will first be described and then the use of the control signals will be described. Thereafter, the manner in which the process measurements are utilized to generate the control signals will be described.

Temperature transducer 61 is representative of a plurality of temperature transducers. Each of the plurality of temperature transducers in combination with temperature measuring devices such as thermocouples, which are operably located at different locations in reactor 27, provide an output signal which is represented as signal 62 and which is representative of the temperature at different locations in the reactor 27. The plurality of signals represented by signal 62 are provided from the plurality of temperature transducers represented by temperature transducer 61 as input signals to computer 100.

In like manner, temperature transducer 64 is representative of a plurality of temperature transducers. Each of the temperature transducers in combination with thermocouples located in different areas of reactor 37 provide a plurality of output signals which are represented by signal 65 and which are representative of the temperature in different areas of the reactor 37. The plurality of signals represented by signal 65 are provided as inputs to computer 100.

Temperature transducer 71 in combination with a temperature sensing device such as a thermocouple, which is operably located in conduit 39, provides an output signal 72 which is representative of the actual temperature of the reaction effluent flowing through conduit 39. Signal 72 is provided from the temperature transducer 71 as an input to computer 100.

In like manner, temperature transducer 74 in combination with a temperature sensing device such as a thermocouple, which is operably located in conduit 45, provides an output signal 76 which is representative of the actual temperature of the fluid flowing through conduit 45. Signal 76 is provided from temperature transducer 74 as an input to computer 100.

Analyzer system 77 is in fluid communication with conduit 39 through conduit 78.

Based on a composition analysis of isopentane ($IC_5$) and normal pentane ($NC_5$) of the reaction effluent flowing through conduit 39, an inferrential measurement of the octane number is provided by analyzer system 77. The octane number is calculated from the equation:

$$OC_m = X_1(OC_{NC5}) + X_2(OC_{IC5}) + A_o$$

where
$X_1$ = mole fraction of $NC_5$
$X_2$ = mole fraction of $IC_5$
$A_o$ = experimentally determined constant
$OC_m$ = octane number of effluent stream
$OC_{NC5}$ = 71.5 RON (Research octane number)
$OC_{IC5}$ = 93.2 RON Thus analyzer system 77 provides an output signal 79 which is representative of the octane number of the reaction effluent flowing through conduit 39. Signal 79 is provided from the analyzer system 77 as an input to computer 100. The analyzer system 77 may be an Optichrom 2100 process chromatograph system from Applied Automation, Bartlesville, Okla.

The constant $A_o$ is determined by making a laboratory determination of the octane number effluent stream for various compositions. Once $OC_m$ is known, $A_o$ can be solved for and used for future, on-line determinations of $OC_m$.

The valve position transducer 81 provided an output signal 82 which is representative of the actual position of control valve 84 which is operably located in conduit 43. Signal 82 is provided from the valve position transducer 81 as an input to computer 100.

In response to the described process measurements and set points which will be described hereinafter, computer 100 establishes three control signals. A description of each of these control signals and its use follows.

Signal 85 is representative of the flow rate of heating fluid through conduit 19 required to insure that the opening of control valve 84 is not reduced below some desired minimum or the temperature of the feed to the separator 47 is not reduced below some desired minimum. Signal 85 is provided as the set point input to the flow controller 86.

Flow transducer 88 in combination with the flow sensor 89, which is operably located in conduit 19, provides an output signal 91 which is representative of the actual flow rate of the heating fluid flowing through conduit 19. Signal 91 is provided from the flow transducer 88 as the process variable input to the flow controller 86.

In response to signals 85 and 91, the flow controller 86 establishes an output signal 92 which is responsive to the difference between signals 85 and 91. Signal 92 is scaled so as to be representative of the position of the control valve 93, which is operably located in conduit 19, required to maintain the actual flow rate of the heating fluid flowing through conduit 19 substantially equal to the desired flow rate represented by signal 85. Signal 92 is provided from the flow controller 86 as a control signal to control valve 93 and control valve 93 is manipulated in response thereto.

Signal 94 is representative of the feed inlet temperature to the reactor 27 required to maintain a desired temperature for the reaction effluent flowing through conduit 39 so as to maintain desired equilibrium reaction conditions in the reactor 37. Signal 94 is provided from computer 100 as the set point input to the temperature controller 96.

Temperature transducer 98 in combination with a temperature sensing device such as a thermocouple, which is operably located in conduit 29, provides an output signal 99 which is representative of the actual feed temperature to the reactor 27. Signal 99 is provided from the temperature transducer 98 as the process variable input to the temperature controller 96.

In response to signals 94 and 99, the temperature controller 96 establishes an output signal 101 which is responsive to the difference between signals 94 and 99. Signal 101 is scaled so as to be representative of the position of the control valve 84 required to maintain the actual feed inlet temperature to reactor 27 substantially equal to the desired feed inlet temperature represented by signal 94. Signal 101 is provided from the temperature controller 96 as a control signal to control valve 84 and control valve 84 is manipulated in response thereto.

Signal 103 is representative of the temperature of the feed flowing through conduit 38 required to maintain a desired differential temperature between the reactor 27 and reactor 37. Signal 103 is provided from computer 100 as the set point input to temperature controller 104.

Temperature transducer 106 in combination with a temperature sensing device such as a thermocouple, which is operably located in conduit 38, provides an output signal 107 which is representative of the actual temperature of the feed flowing through conduit 38. Signal 107 is provided from the temperature transducer 106 as the process variable to the temperature controller 104.

In response to signals 103 and 107, the temperature controller 104 provides an output signal 109 which is responsive to the difference between signals 103 and 107. Signal 109 is scaled so as to be representative of the position of control valve 111, which is operably located in conduit 35, required to maintain the actual differential temperature between reactors 27 and 37 substantially equal to the desired differential temperature represented by signal 103. signal 109 is provided from the temperature controller 104 as a control signal to the control valve 111 and the control valve 111 is manipulated in response thereto.

Referring now to computer 100 and the manner in which the process measurements are utilized to generate the control signals, signal 82, which is representative of the actual position of valve 84, is provided as the process variable input to the valve position controller 121. The valve position controller 121 is also provided with a set point signal 122 which is representative of some minimum desired valve position. Typically, it is undesirable for a control valve to be allowed to go completely shut since it takes much longer to substantially increase flow when a control valve is completely shut as opposed to when a control valve is at least partially open because of the characteristics of control valves. Signal 122 would typically have a value such as 10% open.

In response to signals 82 and 122, the valve position controller 121 provides an output signal 124 which is responsive to the difference between signals 82 and 122. Signal 124 is scaled so as to be representative of the flow rate of heating fluid through conduit 19 required to insure that control valve 84 will remain open by at least a percentage opening represented by signal 122. Signal 124 is provided from the valve position controller 121 as a first input to the high select 126.

Signal 76, which is representative of the actual temperature of the fluid flowing through conduit 45 to the separator 47, is provided as a process variable input to the temperature controller 127. The temperature controller 127 is also provided with a set point signal 128 which is representative of a minimum desired temperature for the feed to the separator 47. While a low temperature for the feed to the separator 47 is desirable to recover additional isomers which would otherwise be lost to recycle, the operating characteristics of the separator 47 will require some minimum feed temperature for proper operation. A typical minimum feed temperature is in the range of about 250° F. to about 350° F.

In response to signals 76 and 128, the temperature controller 127 provides an output signal 129 which is responsive to the difference between signals 76 and 128. Signal 129 is scaled so as to be representative of the flow rate of heating fluid through conduit 19 required to maintain the actual temperature of the feed to the separator 47 substantially equal to the low limit temperature represented by signal 128. Signal 129 is provided from the temperature controller 127 as a second input to the high select 126.

The one of signals 124 and 129 which is representative of the highest flow rate of the heating fluid through conduit 19 is output from the high select 126. Thus, signal 85 will have a magnitude equal to the one of signals 124 and 126 which is representative of the highest flow rate. Signal 85 is provided as a control signal from computer 100 and is utilized as previously described.

It is noted that, if the actual temperature of the feed to the separator 47 is above the minimum temperature represented by signal 128 and if the position of valve 84 is more open than the minimum opening represented by signal 122, the control valve 93 will be held in a closed position. Thus, the heating fluid flowing through conduit 19 is utilized only as required to insure that process constraints are not violated which improves the energy efficiency of the isomerization process.

Signal 72, which is representative of the actual temperature of the reactant effluent flowing through conduit 39, is provided as an input to the calculate temperature set point block 131 and is also provided as the process variable input to the temperature controller 133. Signal 79, which is representative of the actual octane number of the reaction effluent flowing through conduit 39, is also provided as an input to the calculate temperature set point block 131.

In response to signals 72 and 79, the calculate temperature set point block 131 establishes an output signal 134 which is representative of the temperature of the reactant effluent flowing through conduit 39 required to maintain substantially equilibrium reaction conditions for the reactor 37. Signal 134 is provided from the calculate temperature set point block 131 as the set point input to the temperature controller 133.

The manner in which signal 134 is derived is as follows. The equilibrium reaction on which the derivation is based is for pentanes (normal pentane to isopentane).

Figure 3:
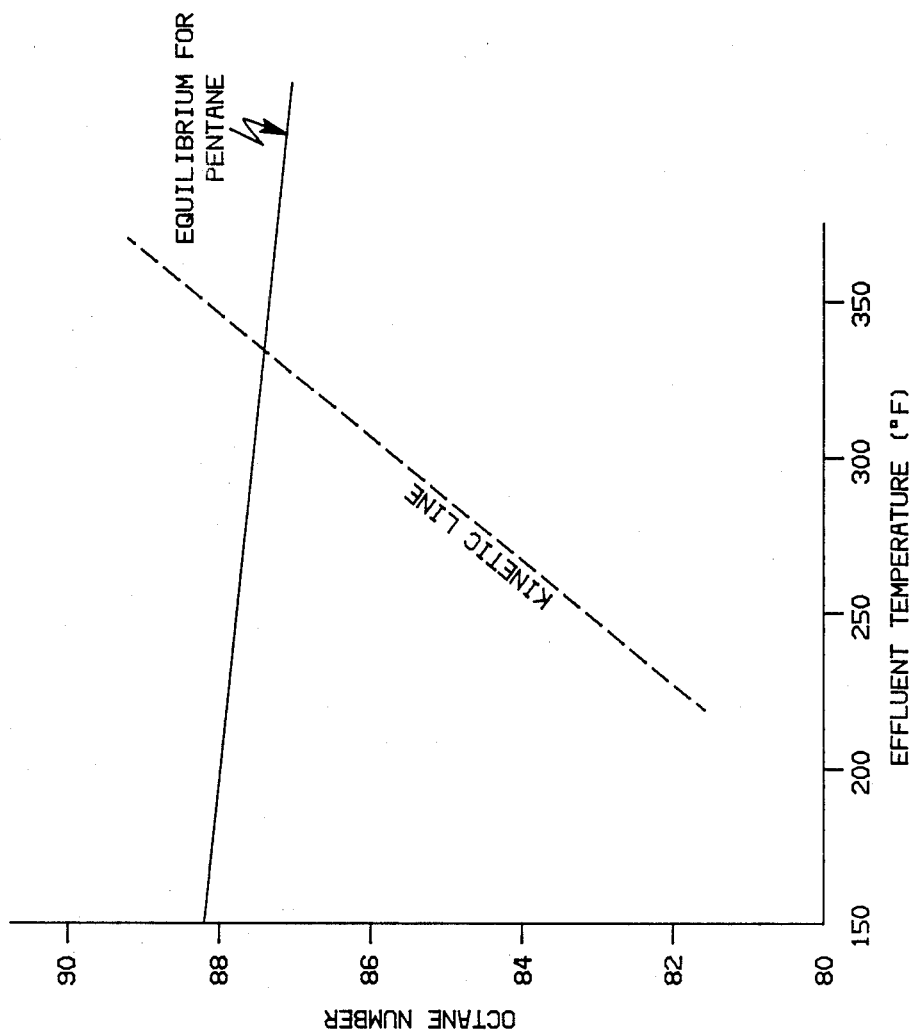
FIG. 3 is a graphical illustration of the relationship between the octane number of the reaction effluent withdrawn from the tail reactor and the temperature of such reaction effluent.
Figure 4:
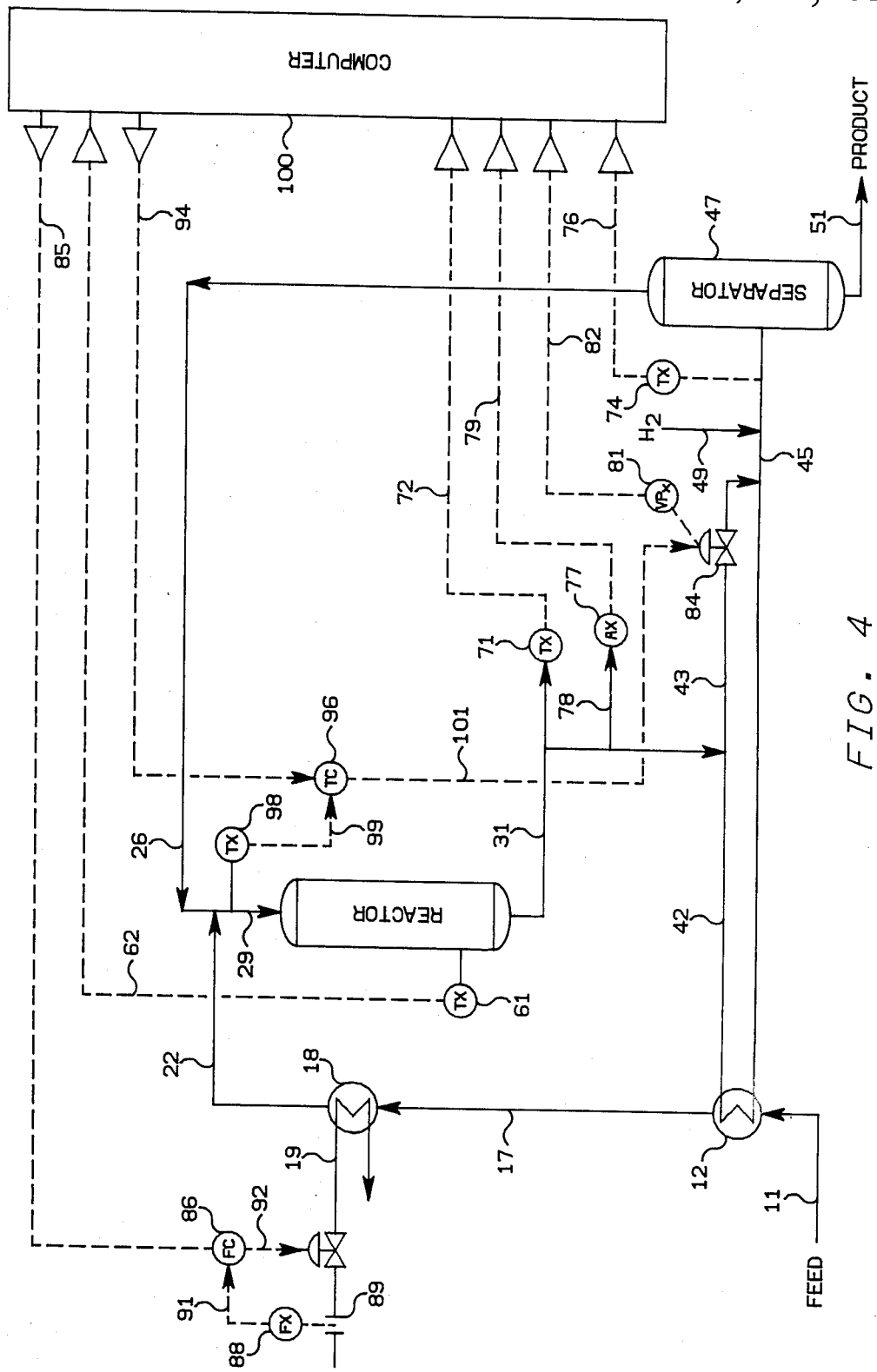
FIG. 4 is a diagramatic illustration of an isomerization process employing a single reactor and the associated control syustem of the present invention.

Referring now to FIG. 3, the relationship between the octane number of the reaction effluent flowing through conduit 39 and the temperature of such reaction effluent is illustrated. The line illustrated as an equilibrium line is a known equilibrium line for pentanes. If the reaction in reactors 27 and 37 is at equilibrium, the operation will be on this line. This line is unique for pentanes.

The dotted line is a kinetic line. If the reaction is not at equilibrium, the operation will be on the kinetic line at a point other than the intersection of the equilibrium line and kinetic line. The kinetic line shifts with coke laydown on the catalyst. The kinetic line is a function of the catalyst used and the reactor used and it is unique for a reactor using a specific catalyst. The kinetic line is established by testing to determine the octane number of the reaction effluent at different temperatures of the reaction effluent.

It is noted that, while the kinetic line will shift as coke is formed on the catalyst, the slope of the kinetic line will remain substantially constant. For the sake of illustration, the slope of the kinetic line illustrated in FIG. 3 has been assumed to be 0.05 octane/degree F. Also, for the sake of illustration, assume that signal 72 has a magnitude of 300° F. Also assume a measured octane number of 85.7.

For the lines illustrated in FIG. 3, equilibrium operation would occur at a temperature of about 340° F. All other operation would be on the kinetic line only, which is undesirable.

The manner in which the equilibrium temperature is calculated once the slope of the kinetic line is known is as follows:

The general form of the kinetic line is given by equation (1):

$$OC - OC_m = 0.05 \ (T - T_m) \tag{1}$$

where
$OC$ = the dependent variable of the graph in FIG. 3;
$OC_m$ = the measured octane number (signal 79);
$T$ = the independent variable of the graph in FIG. 3; and
$T_m$ = the measured temperature of the effluent flowing through conduit 39 (signal 72).

The equation for the equilibrium line is given by equation (2):

$$OC = -0.004T + 88.8 \tag{2}$$

where $OC$ and $T$ are as previously defined.

Rearranging equation (1) gives equation (3):

$$OC = OC_m + 0.05 \ (T - T_m). \tag{3}$$

Combining equations (2) and (3) and rearranging gives $$-0.004T + 88.8 = OC_m + 0.05 \ (T - T_m). \tag{4}$$

Solving for T gives $$T = 1644 - 18.52 \ OC_m + 0.926 \ T_m. \tag{5}$$

Substituting 85.7 for $OC_m$ and 300° F. for gives T equal to about 335° F. which is about the desired result. The result would be exact if the actual measured octane number match 300° F. in FIG. 3. 85.7 is slightly high.

Thus, equation 5 is solved in the calculate temperature set point block 131 to establish the desired temperature set point which is represented by signal 134. It is noted that equation 5 is valid so long as the slope of the kinetic line does not change and the equation of the equilibrium line does not change.

In response to signals 72 and 134, the temperature controller 133 provides output signal 94 which is responsive to the difference between signals 72 and 134. As has been previously stated, signal 94 is scaled so as to be representative of the inlet feed temperature to reactor 27 required to maintain the actual effluent temperature from reactor 37 substantially equal to the desired temperature represented by signal 134. Signal 94 is provided as a control signal from computer 100 and is utilized as has been previously described.

The plurality of temperature measurements represented by signal 62 are provided to the averaging block 141. This plurality of temperature measurements is averaged to establish signal 142 which is representative of the average temperature across the reactor 27. Signal 142 is provided from the averaging block 141 as an input to the subtrahend input of the summing block 144.

In like manner, the plurality of temperature measurements represented by signal 65 are provided as inputs to the averaging block 146. The averaging block 146 establishes an output signal 147 which is representative of the average temperature across the reactor 37. Signal 147 is provided from the averaging block 146 to the minuend input of the summing block 144. Summing block 144 establishes signal 149 which is equal to the difference between signals 147 and 142. Signal 149 is provided as the process variable input to the temperature controller 151.

The temperature controller 151 is also provided with a set point signal 153 which is representative of a desired differential temperature between reactor 27 and reactor 37. A typical differential temperature is 20° F. with reactor 27 being the hotter reactor.

In response to signals 149 and 153, the temperature controller 151 provides an output signal 103 which is responsive to the difference between signals 149 and 153. As has been previously stated, signal 103 is scaled so as to be representative of the temperature of the feed flowing through conduit 38 required to maintain the actual differential temperature between reactors 27 and 37 substantially equal to the desired differential temperature represented by signal 153. Signal 103 is provided as a control signal from computer 100 and is utilized as previously described.

The conditions in reactor 37 are more favorable for isomerization because of operation at a lower temperature and also because the reaction is maintained at equilibrium conditions. The reaction in reactor 27 will typically not be at equilibrium conditions but should be close.

In summary, the isomerization process is controlled so as to substantially maximize the conversion of the feed by maintaining operation at equilibrium conditions and also by maintaining a desired differential temperature between reactors 27 and 37. The energy efficiency of the isomerization process is improved by minimizing the flow of heating fluid through conduit 19. Such minimization also optimizes the separation in separator 47 which allows recovery of additional product that would otherwise be loss to recycle.

As has been previously stated, parts of the invention could be applied to an isomerization process which utilizes only one reactor. The differential temperature control would not be applicable but the equilibrium control could be applied and also the control of the flow of the heating fluid to conduit 19 could be applied. Temperature transducer 71 and analyzer 77 would be on the effluent outlet from the one reactor as opposed to the effluent outlet from a second reactor. In like manner, valve 84 would be for the effluent from the single reactor as opposed to the effluent from the tail reactor 37.

Figure 2:
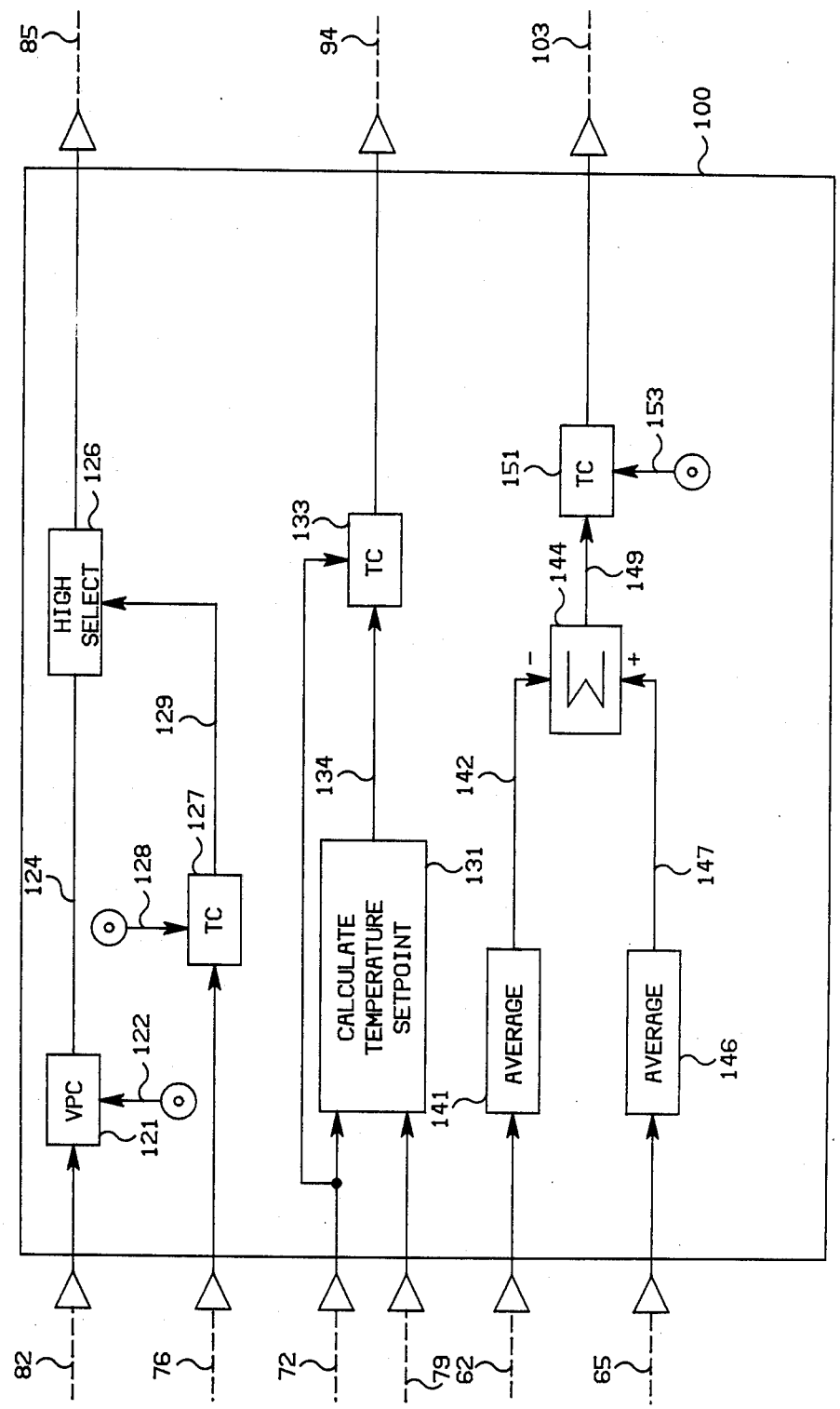
FIG. 2 is a flow diagram of the computer logic utilized to establish the control signals illustrated in FIG. 1 based on the process measurements illustrated in FIG. 1.

The invention has been described in terms of a preferred embodiment as illustrated in FIGS. 1-3. Specific components which can be used in the practice of the invention as illustrated in FIG. 1 such as flow transducer 88; flow sensor 89; flow controller 86; temperature transducers 61, 64, 98, 106, 71 and 74; temperature controllers 96 and 104; valve position transducer 81 and control valves 93, 111 and 84 are each well known commerically available control components such as are illustrated at length in Perry's "Chemical Engineers Handbook", 4th Ed., chapter 22, McGraw-Hill.

It is noted that controllers 86, 96 and 104 could be implemented in computer 100. However, controllers which directly manipulate control valves are typically analog controllers installed on a panel board.

While the invention has been described in terms of the presently preferred embodiment, reasonable variations and modifications are possible by those skilled in the art. Such modifications and variations are within the scope of the described invention and the appended claims.

That which is claimed is:

1. In method for controlling an isomerization process comprising the steps of introducing a feed suitable for isomerization to a feed inlet of a first isomerization reactor, withdrawing a first reaction effluent from said first isomerization reactor, introducing said effluent as a feed to a second isomerization reactor, and withdrawing a second reaction effluent from said second isomerization reactor, wherein the improvement comprises the steps of:

establishing a first signal representative of the actual temperature of said second reaction effluent;

establishing a second signal representative of the actual octane number of said second reaction effluent;

establishing a third signal representative of the temperature of said second reaction effluent required to maintain the isomerization reaction in said second isomerization reactor at equilibrium in response to said first signal and said second signal; and manipulating the temperature of said second reaction effluent in response to said third signal.

2. A method in accordance with claim 1 wherein the improvement further comprises the steps of:

passing said feed through a first heat exchanger before said feed is provided to the feed inlet of said first isomerization reactor;

providing a first poriion of said second reaction effluent as a heating fluid to said first heat exchanger;

passing a second portion of said second reaction effluent through a first control valve, wherein the position of said first control valve determines the amount of said second reaction effluent which is provided as a heating fluid to said first heat exchanger and wherein said step of manipulating the temperature of said second reaction effluent in response to said third signal comprises:

comparing said first signal and said second signal and establishing a fourth signal which is responsive to the difference between said first signal and said third signal, wherein said fourth signal is scaled so as to be representative of the temperature of the feed provided to the feed inlet of said first isomerization reactor required to maintain the actual temperature of said second reaction effluent substantially equal to the desired temperature represented by said third signal;

establishing a fifth signal representative of the actual temperature of the feed provided to the feed inlet of said first isomerization reactor;

comparing said fourth signal and said fifth signal and establishing a sixth signal which is responsive to the difference between said fourth signal and said fifth signal, wherein said sixth signal is scaled so as to be representative of the position of said first control valve required to maintain the actual feed inlet temperature to said first isomerization reactor substantially equal to the desired temperature represented by said fourth signal; and manipulating said first control valve in response to said sixth signal so as to maintain the actual feed inlet temperature to said first isomerization reactor substantially equal to the desired feed inlet temperature represented by said fourth signal which results in the maintenance of the actual temperature of said second reaction effluent substantially equal to the desired temperature represented by said third signal.

3. A method in accordance with claim 2 wherein the improvement further comprises the steps of:

passing said feed through a second heat exchanger before said feed is provided to the feed inlet of said first isomerization reactor;

providing a first portion of said first reaction effluent as a heating fluid to said second heat exchanger;

passing a second portion of said first reaction effluent through a second control valve, wherein the position of said second control valve determines the amount of said first reaction effluent which is provided as a heating fluid to said second heat exchanger;

combining said first portion of said first reaction effluent and said second portion of said first reaction effluent and for providing the thus combined first and second portions of said first reaction effluent as the feed to said second isomerization reactor;

establishing a seventh signal representative of the average temperature across said first isomerization reactor;

establishing an eighth signal representative of the average temperature across said second isomerization reactor;

subtracting said seventh signal from said eighth signal to establish a ninth signal representative of the difference in the temperature across said first isomerization reactor and said second isomerization reactor;

establishing a tenth signal representative of a desired difference between the temperature across said first isomerization reactor and the temperature across said second isomerization reactor;

comparing said ninth signal and said tenth signal and establishing an eleventh signal which is responsive to the difference between said the said ninth signal and said tenth signal, wherein said eleventh signal is scaled so as to be representative of the temperature of the feed provided to the feed inlet of said second isomerization reactor required to maintain the actual difference between the temperature across said first reactor and the temperature across said second reactor substantially equal to the desired difference represented by said tenth signal; and manipulating the temperature of the feed provided to said second isomerization reactor in response to said eleventh signal.

4. A method in accordance with claim 3 wherein the improvement further comprises that said step of manipulating the temperature of the feed provided to the feed inlet of said second isomerization reactor in response to said eleventh signal comprises:

establishing a twelfth signal representative of the actual temperature of the feed provided to the feed inlet of said second isomerization reactor;

comparing said eleventh signal and said twelfth signal and establishing a thirteenth signal which is responsive to the difference between said eleventh signal and said twelfth signal, wherein said thirteenth signal is scaled so as to be representative of the position of said second control valve required to maintain the actual temperature of the feed provided to the feed inlet of said second isomerization reactor substantially equal to the desired temperature represented by said eleventh signal; and manipulating said second control valve in response to said thirteenth signal.

5. A method in accordance with claim 3 wherein the improvement further comprises the steps of:

providing a heating fluid to a third heat exchanger;

passing said feed through said third heat exchanger before said feed is provided to the feed inlet of said first isomerization reactor;

combining the first portion and second portion of said second reaction effluent and providing the thus combined first portion and second portion of said second reaction effluent as a feed to a separator;

establishing a twelfth signal representative of the actual position of said first control valve;

establishing a thirteenth signal representative of a desired minimum opening for said first control valve;

comparing said twelfth signal and said thirteenth signal and establishing a fourteenth signal which is responsive to the difference between said twelfth signal and said thirteenth signal, wherein said fourteenth signal is scaled so as to be representative of the flow rate of said heating fluid required to maintain the actual position of said first control valve substantially equal to the desired minimum open position represented by said thirteenth signal;

establishing a fifteenth signal representative of the actual temperature of the feed provided to said separator;

establishing a sixteenth signal representative of a low limit on the temperature of the feed provided to said separator;

comparing said fifteenth signal and said sixteenth signal and establishing a seventeenth signal which is responsive to the difference between said fifteenth signal and said sixteenth signal, wherein said seventeenth signal is scaled so as to be representative of the flow rate of said heating fluid required to maintain the actual temperature of the feed provided to said separator substantially equal to the low limit temperature represented by said sixteenth signal;

establishing an eighteenth signal which is equal to the one of said fourteenth and said seventeenth signals which is representative of the highest flow rate of said heating fluid; and manipulating the flow rate of said heating fluid in response to said eighteenth signal.

6. A method in accordance with claim 5 wherein the improvement further comprises that said step of manipulating the flow rate of said heating fluid in response to said eighteenth signal comprises:

establishing a nineteenth signal representative of the actual flow rate of said heating fluid;

comparing said eighteenth signal and said nineteenth signal and establishing a twentieth signal which is responsive to the difference between said eighteenth signal and said nineteenth signal, wherein said twentieth signal is scaled so as to be representative of the position of a third control valve, operably located so as to control the flow of said heating fluid, required to maintain the actual flow rate of said heating fluid substantially equal to the desired flow rate represented by said eighteenth signal; and manipulating said third control valve in response to said twentieth signal.

7. In method for controlling an isomerization process comprising the steps of introducing a feed suitable for isomerization to the feed inlet of an isomerization reactor and withdrawing a reaction effluent from said isomerization reactor, wherein the improvement further comprises the steps of:

establishing a first signal representative of the actual temperature of said reaction effluent;

establishing a second signal representative of the actual octane number of said reaction effluent;

establishing a third signal representative of the temperature of said reaction effluent required to maintain the isomerization reaction in said isomerization reactor at equilibrium in response to said first signal and said second signal; and manipulating the temperature of said reaction effluent in response to said third signal.

8. A method in accordance with claim 7 wherein the improvement further comprises the steps of:

passing said feed through a first heat exchanger before said feed is provided to the feed inlet of said first isomerization reactor;

providing a first portion of said reaction effluent as a heating fluid to said first heat exchanger;

passing a second portion of said reaction effluent through a first control valve, wherein the position of said first control valve determines the amount of said reaction effluent which is provided as a heating fluid to said first heat exchanger and wherein said step of manipulating the temperature of said reaction effluent in response to said third signal comprises:

comparing said first signal and said second signal and establishing a fourth signal which is responsive to the difference between said first signal and said third signal, wherein said fourth signal is scaled so as to be representative of the temperature of the feed provided to the feed inlet of said isomerization reactor required to maintain the actual temperature of said reaction effluent substantially equal to the desired temperature represented by said third signal;

establishing a fifth signal representative of the actual temperature of the feed provided to the feed inlet of said isomerization reactor;

comparing said fourth signal and said fifth signal and for establishing a sixth signal which is responsive to the difference between said fourth signal and said fifth signal, wherein said sixth signal is scaled so as to be representative of the position of said first control valve required to maintain the actual feed inlet temperature to said isomerization reactor substantially equal to the desired temperature represented by said fourth signal; and manipulating said first control valve in response to said sixth signal so as to maintain the actual feed inlet temperature to said isomerization reactor substantially equal to the desired feed inlet temperature represented by said fourth signal which results in the maintenance of the actual temperature of said reaction effluent substantially equal to the desired temperature represented by said third signal.

9. A method in accordance in claim 8 wherein the improvement further comprises the steps of:

providing a heating fluid to a second heat exchanger;

passing said feed through said second heat exchanger before said feed is provided to the feed inlet of said isomerization reactor;

combining the first portion and second portion of said reaction effluent and providing the thus combined first portion and second portion of said reaction effluent as a feed to a separator;

establishing a seventh signal representative of the actual position of said first control valve;

establishing an eighth signal representative of a desired minimum opening for said first control valve;

comparing said seventh signal and said eighth signal and establishing a ninth signal which is responsive to the difference between said seventh signal and said eighth signal, wherein said ninth signal is scaled so as to be representative of the flow rate of said heating fluid required to maintain the actual position of said first control valve substantially equal to the desired minimum open position represented by said eighth signal;

establishing a tenth signal representative of the actual emperature of the feed provided to said separator;

establishing an eleventh signal representative of a low limit on the temperature of the feed provided to said separator;

comparing said tenth signal and said eleventh signal and establishing a twelfth signal which is responsive to the difference between said tenth signal and said eleventh signal wherein said twelfth signal is scaled so as to be representative of the flow rate of said heating fluid required to maintain the actual temperature of the feed provided to said separator substantially equal to the low limit temperature represented by said eleventh signal;

establishing a thirteenth signal which is equal to the one of said ninth and said twelfth signals which is representative of the highest flow rate of said heating fluid; and manipulating the flow rate of said heating fluid in response to said thirteenth signal.

10. A method in accordance with the claim 9 wherein the improvement further comprises that said step of manipulating the flow rate of said heating fluid in response to said thirteenth signal comprises:

establishing a fourteenth signal representative of the actual flow rate of said heating fluid;

comparing said thirteenth signal and said fourteenth signal and establishing a fifteenth signal which is responsive to the difference between said thirteenth signal and said fourteenth signal, wherein said fifteenth signal is scaled so as to be representative of the position of a second control valve, operably located so as to control the flow of said heating fluid, required to maintain the actual flow rate of said heating fluid substantially equal to the desired flow rate represented by said thirteenth signal; and manipulating said second control valve in response to said fifteenth signal.

11. Apparatus comprising:

a first isomerization reactor including a feed inlet and an effluent outlet;

a second isomerization reactor including a feed inlet and an effluent outlet;

means for providing a feed suitable for isomerization to said feed inlet within said first isomerization reactor;

means for withdrawing a first reaction effluent from said first isomerization reactor and for providing said first reaction effluent as a feed to said second isomerization reactor;

means for withdrawing a second reaction effluent from said second isomerization reactor;

means for establishing a first signal representative of the actual temperature of said second reaction effluent;

means for establishing a second signal representative of the actual octane number of said second reaction effluent;

means for establishing a third signal representative of the temperature of said second reaction effluent required to maintain the isomerization reaction in said second isomerization reactor at equilibrium in response to said first signal and said second signal; and means for manipulating the temperature of said second reaction effluent in response to said third signal.

12. Apparatus in accordance with claim 11 additionally comprising:

a first heat exchanger;

means for passing said feed through said first heat exchanger before said feed is provided to the feed inlet of said first isomerization reactor;

means for providing a first control valve; a first portion of said second reaction effluent as a heating fluid to said first heat exchanger and for passing a second portion of said second reaction effluent through said first control valve, wherein the position of said first control valve determines the amount of said second reaction effluent which is provided as a heating fluid to said first heat exchanger and wherein said means for manipulating the temperature of said second reaction effluent in response to said third signal comprises:

means for comparing said first signal and said third signal and for establishing a fourth signal which is responsive to the difference between said first signal and said third signal, wherein said fourth signal is scaled so as to be representative of the temperature of the feed provided to the feed inlet of said first isomerization reactor required to maintain the actual temperature of said second reaction effluent substantially equal to the desired temperature represented by said third signal;

means for establishing a fifth signal representative of the actual temperature of the feed provided to the feed inlet of said first isomerization reactor;

means for comparing said fourth signal and said fifth signal and for establishing a sixth signal which is responsive to the difference between said fourth signal and said fifth signal, wherein said sixth signal is scaled so as to be representative of the position of said first control valve required to maintain the actual feed inlet temperature to said first isomerization reactor substantially equal to the desired temperature represented by said fourth signal; and means for manipulating said first control valve in response to said sixth signal so as to maintain the actual feed inlet temperature to said first isomerization reactor substantially equal to the desired feed inlet temperature represented by said fourth signal which results in the maintenance of the actual temperature of said second reaction effluent substantially equal to the desired temperature represented by said third signal.

13. Apparatus in accordance with claim 12 additionally comprising:

a second heat exchanger;

means for passing said feed through said second heat exchanger before said feed is provided to the feed inlet of said first isomerization reactor;

a second control valve;

means for providing a first portion of said first reaction effluent as a heating fluid to said second heat exchanger and for passing a second portion of said first reaction effluent through said second control valve, wherein the position of said second control valve determines the amount of said first reaction effluent which is provided as a heating fluid to said second heat exchanger;

means for combining said first portion of said first reaction effluent and said second portion of said first reaction effluent and for providing the thus combined first and second portions of said first reaction effluent as the feed to said second isomerization reactor;

means for establishing a seventh signal representative of the average temperature across said first isomerization reactor;

means for establishing an eighth signal representative of the average temperature across said second isomerization reactor;

means for subtracting said seventh signal from said eighth signal to establish a ninth signal representative of the difference in the temperature across said first isomerization reactor and said second isomerization reactor;

means for establishing a tenth signal representative of a desired difference between the temperature across said first isomerization reactor and the temperature across said second isomerization reactor;

means for comparing said ninth signal and said tenth signal and for establishing an eleventh signal which is responsive to the difference between said the said ninth signal and said tenth signal, wherein said eleventh signal is scaled so as to be representative of the temperature of the feed provided to the feed inlet of said second isomerization reactor required to maintain the actual difference between the temperature across said first reactor and the temperature across said second reactor substantially equal to the desired difference represented by said tenth signal; and means for manipulating the temperature of the feed provided to said second isomerization reactor in response to said eleventh signal.

14. Apparatus in accordance with claim 13 wherein said means for manipulating the temperature of the feed provided to the feed inlet of said second isomerization reactor in response to said eleventh signal comprises:

means for establishing a twelfth signal representative of the actual temperature of the feed provided to the feed inlet of said second isomerization reactor;

means for comparing said eleventh signal and said twelfth signal and for establishing a thirteenth signal which is responsive to the difference between said eleventh signal and said twelfth signal, wherein said thirteenth signal is scaled so as to be representative of the position of said second control valve required to maintain the actual temperature of the feed provided to the feed inlet of said second isomerization reactor substantially equal to the desired temperature represented by said eleventh signal; and means for manipulating said second control valve in response to said thirteenth signal.

15. Apparatus in accordance with claim 13 additionally comprising:

a third heat exchanger;

means for providing a heating fluid to said third heat exchanger;

means for passing said feed through said third heat exchanger before said feed is provided to the feed inlet of said first isomerization reactor;

a separator;

means for combining the first portion and second portion of said second reaction effluent and for providing the thus combined first portion and second portion of said second reaction effluent as a feed to said separator;

means for establishing a twelfth signal representative of the actual position of said first control valve;

means for establishing a thirteenth signal representative of a desired minimum opening for said first control valve;

means for comparing said twelfth signal and said thirteenth signal and for establishing a fourteenth signal which is responsive to the difference between said twelfth signal and said thirteenth signal, wherein said fourteenth signal is scaled so as to be representative of the flow rate of said heating fluid required to maintain the actual position of said first control valve substantially equal to the desired minimum open position represented by said thirteenth signal;

means for establishing a fifteenth signal representative of the actual temperature of the feed provided to said separator;

means for establishing a sixteenth signal representative of a low limit on the temperature of the feed provided to said separator;

means for comparing said fifteenth signal and said sixteenth signal and for establishing a seventeenth signal which is responsive to the difference between said fifteenth signal and said sixteenth signal, wherein said seventeenth signal is scaled so as to be representative of the flow rate of said heating fluid required to maintain the actual temperature of the feed provided to said separator substantially equal to the low limit temperature represented by said sixteenth signal;

a high select means;

means for providing said fourteenth signal and said seventeenth signal to said high select means, wherein said high select means establishes an eighteenth signal which is equal to the one of said fourteenth and said seventeenth signals which is representative of the highest flow rate of said heating fluid; and means for manipulating the flow rate of said heating fluid in response to said eighteenth signal.

16. Apparatus in accordance with claim 15 wherein said means for manipulating the flow rate of said heating fluid in response to said eighteenth signal comprises:

a third control valve operably located so as to control the flow of said heating fluid;

means for establishing a nineteenth signal representative of the actual flow rate of said heating fluid;

means for comparing said eighteenth signal and said nineteenth signal and for establishing a twentieth signal which is responsive to the difference between said eighteenth signal and said nineteenth signal, wherein said twentieth signal is scaled so as to be representative of the position of said third control valve required to maintain the actual flow rate of said heating fluid substantially equal to the desired flow rate represented by said eighteenth signal; and means for manipulating said third control valve in response to said twentieth signal.

17. Apparatus comprising:

an isomerization reactor including a feed inlet and an effluent outlet;

means for providing a feed suitable for isomerization to said feed inlet of said isomerization reactor;

means for withdrawing a reaction effluent from said isomerization reactor;

means for establishing a first signal representative of the actual temperature of said reaction effluent;

means for establishing a second signal representative of the actual octane number of said reaction effluent;

means for establishing a third signal representative of the temperature of said reaction effluent required to maintain the isomerization reaction in said isomerization reactor at equilibrium in response to said first signal and said second signal; and means for manipulating the temperature of said reaction effluent in response to said third signal.

18. Apparatus in accordance with claim 17 additionally comprising:

a first heat exchanger;

means for passing said feed through said first heat exchanger before said feed is provided to the feed inlet of said isomerization reactor;

a first control valve;

means for providing a first portion of said reaction effluent as a heating fluid to said first heat exchanger and for passing a second portion of said reaction effluent through said first control valve, wherein the position of said first control valve determines the amount of said reaction effluent which is provided as a heating fluid to said first heat exchanger and wherein said means for manipulating the temperature of said reaction effluent in response to said third signal comprises:

means for comparing said first signal and said third signal and for establishing a fourth signal which is responsive to the difference between said first signal and said third signal, wherein said fourth signal is scaled so as to be representative of the temperature of the feed provided to the feed inlet of said isomerization reactor required to maintain the actual temperature of said reaction effluent substantially equal to the desired temperature represented by said third signal;

means for establishing a fifth signal representative of the actual temperature of the feed provided to the feed inlet of said isomerization reactor;

means for comparing said fourth signal and said fifth signal and for establishing a sixth signal which is responsive to the difference between said fourth signal and said fifth signal, wherein said sixth signal is scaled so as to be representative of the position of said first control valve required to maintain the actual feed inlet temperature to said isomerization reactor substantially equal to the desired temperature represented by said fourth signal; and means for manipulating said first control valve in response to said sixth signal so as to maintain the actual feed inlet temperature to said isomerization reactor substantially equal to the desired feed inlet temperature represented by said fourth signal which results in the maintenance of the actual temperature of said reaction effluent substantially equal to the desired temperature represented by said third signal.

19. Apparatus in accordance in claim 18 additionally comprising:

a second heat exchanger;

means for providing a heating fluid to said second heat exchanger;

means for passing said feed through said second heat exchanger before said feed is provided to the feed inlet of said isomerization reactor;

a separator;

means for combining the first portion and second portion of said reaction effluent and for providing the thus combined first portion and second portion of said reaction effluent as a feed to said separator;

means for establishing a seventh signal representative of the actual position of said first control valve;

means for establishing an eighth signal representative of a desired minimum opening for said first control valve;

means for comparing said seventh signal and said eighth signal and for establishing a ninth signal which is responsive to the difference between said seventh signal and said eighth signal, wherein said ninth signal is scaled so as to be representative of the flow rate of said heating fluid required to maintain the actual position of said first control valve substantially equal to the desired minimum open position represented by said eighth signal;

means for establishing a tenth signal representative of the actual temperature of the feed provided to said separator;

means for establishing an eleventh signal representative of a low limit on the temperature of the feed provided to said separator;

means for comparing said tenth signal and said eleventh signal and for establishing a twelfth signal which is responsive to the difference between said tenth signal and said eleventh signal, wherein said twelfth signal is scaled so as to be representative of the flow rate of said heating fluid required to maintain the actual temperature of the feed provided to said separator substantially equal to the low limit temperature represented by said eleventh signal;

a high select means;

means for providing said ninth signal and said twelfth signal to said high select means, wherein said high select means establishes a thirteenth signal which is equal to the one of said ninth and said twelfth signals which is representative of the highest flow rate of said heating fluid; and means for manipulating the flow rate of said heating fluid in response to said thirteenth signal.

20. Apparatus in accordance with claim 19 wherein said means for manipulating the flow rate of said heating fluid in response to said thirteenth signal comprises:

a second control valve operably located so as to control the flow of said heating fluid;

means for establishing a fourteenth signal representative of the actual flow rate of said heating fluid;

means for comparing said thirteenth signal and said fourteenth signal and for establishing a fifteenth signal which is responsive to the difference between said thirteenth signal and said fourteenth signal, wherein said fifteenth signal is scaled so as to be representative of the position of said second control valve required to maintain the actual flow rate of said heating fluid substantially equal to the desired flow rate represented by said thirteenth signal; and means for manipulating said second control valve in response to said fifteenth signal.

* * * * *